(12) United States Patent
Hattori et al.

(10) Patent No.: US 11,901,074 B2
(45) Date of Patent: Feb. 13, 2024

(54) MEDICAL INFORMATION PROCESSING APPARATUS, MEDICAL INFORMATION PROCESSING METHOD, AND NON-TRANSITORY COMPUTER-READABLE STORAGE MEDIUM STORING PROGRAM

(71) Applicant: CANON MEDICAL SYSTEMS CORPORATION, Otawara (JP)

(72) Inventors: Chihiro Hattori, Nasushiobara (JP); Takuya Sakaguchi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 542 days.

(21) Appl. No.: 17/130,230

(22) Filed: Dec. 22, 2020

(65) Prior Publication Data

US 2021/0201482 A1 Jul. 1, 2021

(30) Foreign Application Priority Data

Dec. 26, 2019 (JP) ................................. 2019-235966

(51) Int. Cl.
*G06T 7/00* (2017.01)
*G16H 50/20* (2018.01)
(Continued)

(52) U.S. Cl.
CPC ............. *G16H 50/20* (2018.01); *G06F 18/22* (2023.01); *G06T 7/0012* (2013.01);
(Continued)

(58) Field of Classification Search
CPC ........ G16H 50/20; G16H 10/60; G06F 18/22; G06T 7/0012
See application file for complete search history.

(56) References Cited

U.S. PATENT DOCUMENTS

2006/0247502 A1* 11/2006 Chen ...................... G06V 40/10
600/407
2015/0238148 A1* 8/2015 Georgescu .............. G06F 18/28
600/408
(Continued)

FOREIGN PATENT DOCUMENTS

JP 2019-40365 A 3/2019
JP 2019-509813 A 4/2019
WO WO 2016/111014 A1 7/2016

OTHER PUBLICATIONS

Japanese Office Action dated Jun. 20, 2023 in Japanese Application 2019-235966, 3 pages.

*Primary Examiner* — Edward Park
(74) *Attorney, Agent, or Firm* — Oblon, McClelland, Maier & Neustadt, L.L.P.

(57) ABSTRACT

In one embodiment, a medical information processing apparatus includes processing circuitry configured to: perform processing using a trained model that is generated by machine learning with a plurality of training data; acquire first attribute data indicating an attribute of an object-to-be-trained related to the plurality of training data that are used for generating the trained model; acquire second attribute data indicating an attribute of an object-to-be-diagnosed; and perform the processing on input-data of the object-to-be-diagnosed based on goodness of fit that is an index indicating degree of matching between the first attribute data and the second attribute data.

11 Claims, 10 Drawing Sheets

(51) Int. Cl.
*G16H 10/60* (2018.01)
*G06F 18/22* (2023.01)
*G06V 10/74* (2022.01)
*G06V 10/764* (2022.01)

(52) U.S. Cl.
CPC .......... *G06V 10/761* (2022.01); *G06V 10/764* (2022.01); *G16H 10/60* (2018.01); *G06T 2207/20081* (2013.01)

(56) References Cited

U.S. PATENT DOCUMENTS

| | | | |
|---|---|---|---|
| 2016/0232423 A1* | 8/2016 | Zhong | B60H 1/00735 |
| 2018/0174046 A1* | 6/2018 | Xiao | G06F 18/24133 |
| 2019/0236782 A1* | 8/2019 | Amit | G06T 7/0016 |
| 2020/0020097 A1* | 1/2020 | Do | G06F 18/2413 |
| 2020/0110532 A1* | 4/2020 | Mani | H04N 23/611 |
| 2020/0152326 A1* | 5/2020 | Sanchez-Martin | G16H 50/20 |
| 2020/0286228 A1* | 9/2020 | Guenther | G06T 7/0012 |
| 2021/0142908 A1* | 5/2021 | Lahrmann | G06V 10/82 |
| 2023/0144621 A1* | 5/2023 | Enten | G06T 7/0002 351/206 |

* cited by examiner

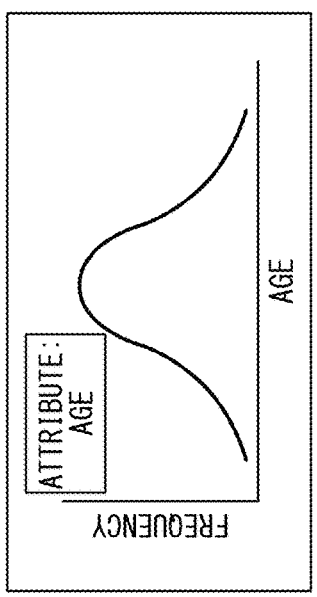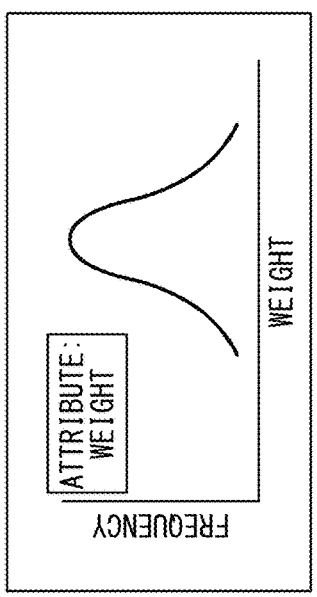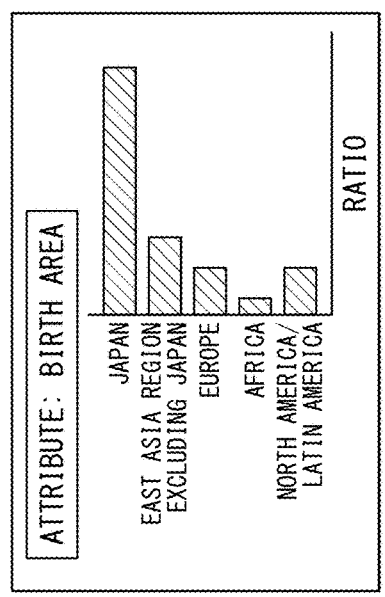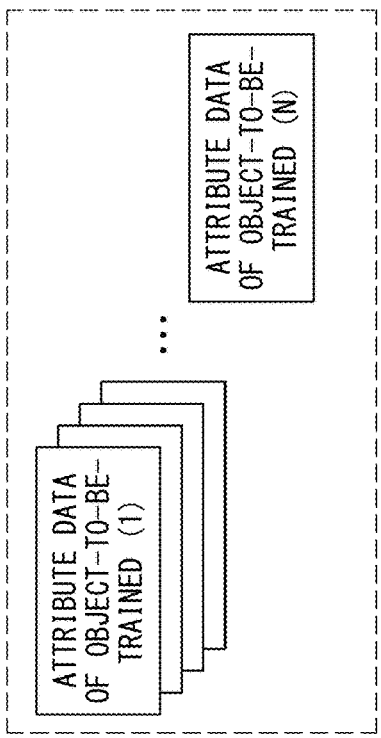

SC1

SELECTION OF ATTRIBUTE OF OBJECT

- ☑ AGE
- ☑ DEGREE OF OBESITY
- ☐ GENDER
- ☑ WEIGHT
- ☑ BLOOD PRESSURE
- ☑ BIRTH AREA
- ☐ HEIGHT
- ☐ BLOOD GLUCOSE LEVEL
- ☐ RACE

⋮  ⋮  ⋮

SELECT

FIG. 9

MEDICAL INFORMATION PROCESSING APPARATUS, MEDICAL INFORMATION PROCESSING METHOD, AND NON-TRANSITORY COMPUTER-READABLE STORAGE MEDIUM STORING PROGRAM

CROSS-REFERENCE TO RELATED APPLICATION

This application is based upon and claims the benefit of priority from Japanese Patent Application No. 2019-235966, filed on Dec. 26, 2019, the entire contents of which are incorporated herein by reference.

FIELD

Disclosed embodiments relate to a medical information processing apparatus, a medical information processing method, and a non-transitory computer-readable storage medium storing a medical information processing program.

BACKGROUND

Today, application of technology using machine learning is being promoted in the fields of diagnosis and examination based on medical images. For example, machine learning, using a large number of medical images that are generated by imaging an object with a modality such as an X-ray CT (Computed Tomography) apparatus, an MRI (Magnetic Resonance Imaging) apparatus, and an ultrasonic diagnostic apparatus, is conducted. By applying a medical image of a new object to a trained model obtained by the machine learning, medical support information such as diagnosis and treatment regarding the new object can be obtained.

A process to generate a trained model is called a training phase, and a process to use the trained model is called a running phase. The training phase is sometimes called a learning phase, and the running phase is sometimes called a utilization phase or an inference phase. In general, the number of data (e.g., medical images) and/or attributes of those data used in the training phase affect the accuracy of the trained model.

For example, assuming there is a case where a trained model is generated using medical images of objects diagnosed at a certain hospital. The hospital should accept objects (or patients) of different races and ages. However, in reality, the trained model is often generated by learning using medical images of objects sampled only from a population having a specific attribute, for example, medical images of objects of adult Japanese.

In such a case, medical images of an object belonging to a population that is not used for training (e.g., medical images of a child and/or a foreigner) are applied to the trained model generated from adult Japanese. Consequently, the correct diagnosis result (e.g., the correct disease name) may not be obtained. In other words, if the attributes of the population of the objects depicted in the medical images which have been used to generate the trained model in the learning phase are different from the attributes of the population of the object depicted in the medical image used in the running phase, the trained model may not provide a correct diagnostic result, and consequently, there is a possibility that the trained model provides incorrect diagnostic support information.

BRIEF DESCRIPTION OF THE DRAWINGS

In the accompanying drawings:

FIG. 5A to FIG. 5D are schematic diagrams illustrating an operation concept of the training phase;

FIG. 9 is a schematic diagram illustrating a display screen for selecting an attribute type to be used for determination.

DETAILED DESCRIPTION

In one embodiment, a medical information processing apparatus includes processing circuitry configured to: perform processing using a trained model that is generated by performing machine learning with a plurality of training data; acquire first attribute data indicating at least one attribute of an object-to-be-trained related to the plurality of training data that are used for generating the trained model; acquire second attribute data indicating at least one attribute of an object-to-be-diagnosed; and perform the processing using the trained model on input-data of the object-to-be-diagnosed based on goodness of fit that is an index indicating degree of matching between the first attribute data and the second attribute data.

Hereinafter, embodiments of a medical information processing apparatus will be described by referring to the accompanying drawings. In the following embodiments, the components with the same reference signs are assumed to have the same configuration and operate in the same manner, and duplicate description is omitted as appropriate.

Figure 1:
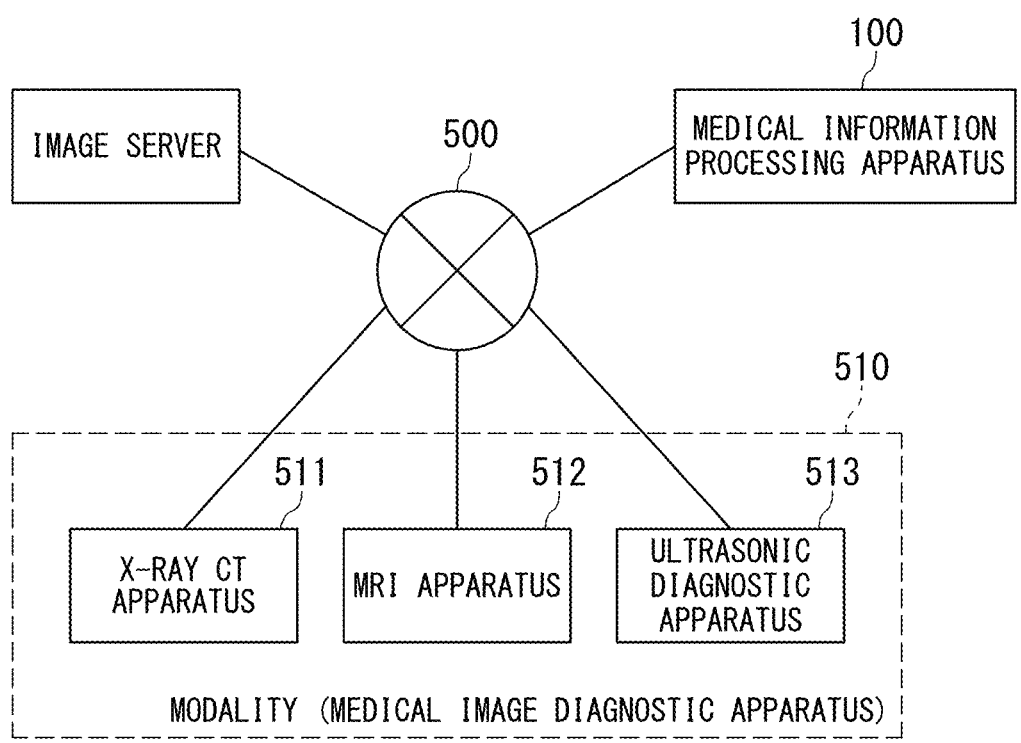
FIG. 1 is a schematic diagram illustrating a configuration of a medical information processing system that includes a medical information processing apparatus of the present embodiment.

FIG. 1 is a schematic diagram illustrating a configuration of a medical information processing system including the medical information processing apparatus 100 of the present embodiment. The medical information processing system is, for example, a system performing series of processing, which are related to medical images, that acquire, process, store, and use the medical images in a hospital.

The medical information processing system includes: an image server; the medical information processing apparatus 100; and a modality 510 (i.e., medical image diagnostic apparatus 510) for acquiring medical images from an object such as a patient. The modality may be, for example, an X-ray CT apparatus 511, an MRI apparatus 512, and an ultrasonic diagnostic apparatus 513. Each of these components or apparatuses is interconnected, for example, via an in-hospital network 500 such that various data and medical images can be exchanged. The medical information processing apparatus 100 can acquire the medical images outputted from the modality 510 and the medical images stored in the image server. Further, the medical information processing apparatus 100 can acquire, as input data, biological information of an object such as a respiratory signal and/or a body motion signal outputted from an electrocardiograph or a pulse wave meter (not shown). In addition, the medical information processing apparatus 100 can also acquire raw data such as projection data for reconstructing a CT image and k-space data for reconstructing an MRI image from the X-ray CT apparatus 511 and the MRI apparatus 512.

(Configuration of Medical Information Processing Apparatus)

Figure 2:
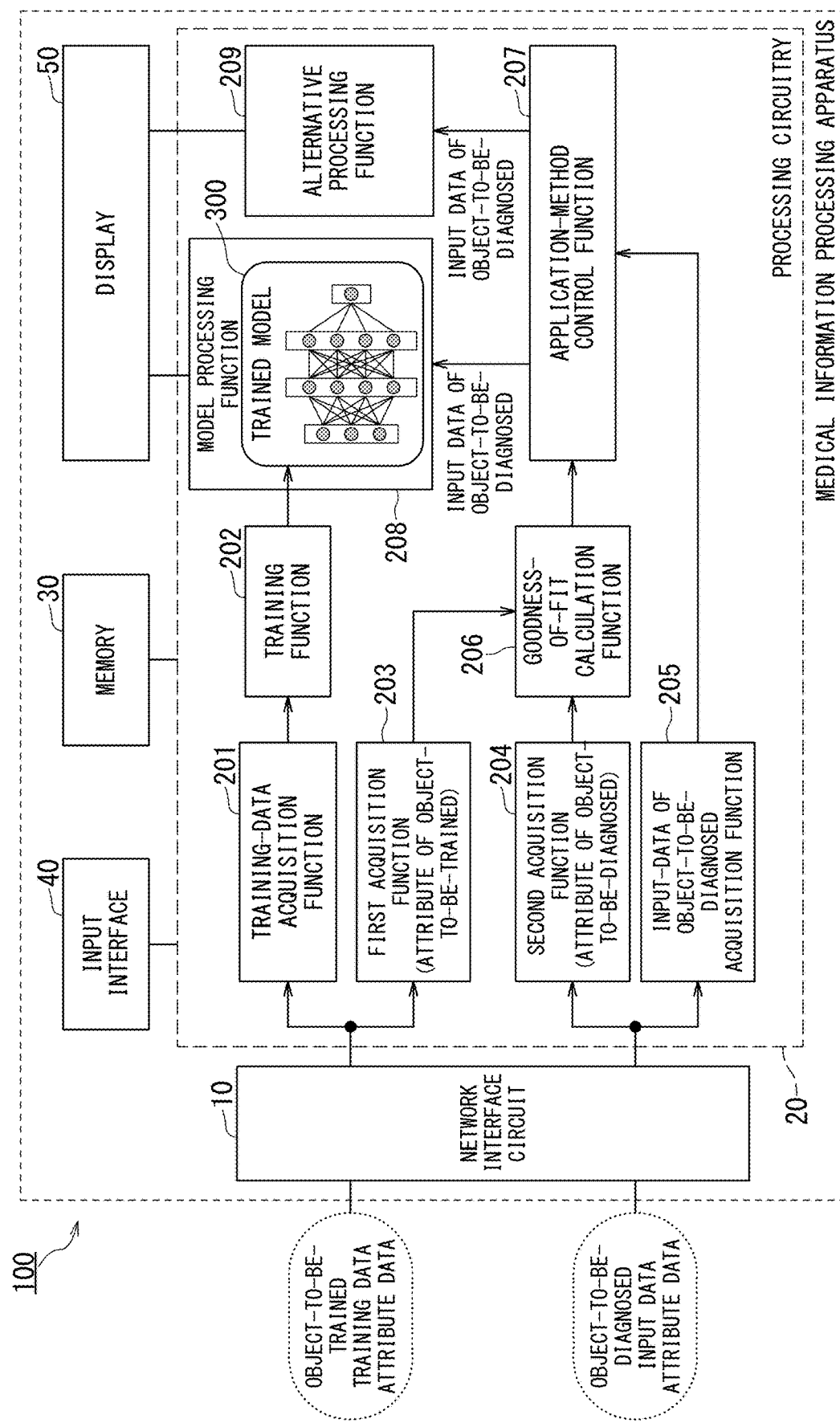
FIG. 2 is a block diagram illustrating a configuration of the medical information processing apparatus of the present embodiment.

FIG. 2 is a block diagram illustrating a configuration of the medical information processing apparatus 100 according to the present embodiment. The medical information processing apparatus 100 includes: a network interface circuit 10; processing circuitry 20; a memory 30; an input interface 40; and a display 50, for example. The medical information processing apparatus 100 is configured as, for example, a so-called workstation or a high-performance personal computer.

The network interface circuit 10 is an interface circuit for acquiring data via a wired or wireless network and/or for acquiring data via a portable storage medium such as an optical disk and a USB memory. The network interface circuit 10 may acquire data via the in-hospital network 500 shown in FIG. 1 or may acquire data from a medical institution outside the hospital via the internet or a public communication line.

The memory 30 is a recording medium including a read-only memory (ROM) and a random-access memory (RAM) in addition to an external memory device such as a hard disk drive (HDD) and an optical disc device. The memory 30 stores various data and information including a trained model described below and attribute data of an object to be trained (hereafter, object(s)-to-be-trained). Further, the memory 30 stores various programs to be executed by the processor included in the processing circuitry 20.

The input interface 40 includes various devices for an operator to input various data and information, and may be configured as a mouse, a keyboard, a trackball, and/or a touch panel, for example.

The display 50 is a display device such as a liquid crystal display panel, a plasma display panel, and/or an organic EL panel.

The processing circuitry 20 is a circuit that includes a central processing unit (CPU) and/or a special-purpose or general-purpose processor, for example. The processor implements various functions described below by executing the programs stored in the memory 30. The processing circuitry 20 may be configured as hardware such as an FPGA (field programmable gate array) and/or an ASIC (application specific integrated circuit). The various functions described below can also be implemented by such hardware. Additionally, the processing circuitry 20 can implement the various functions by combining hardware processing and software processing based on its processor and programs.

Further, the processing circuitry 20 may be configured by combining a plurality of independent processors such that the processors implement the respective functions. When the processing circuitry 20 is provided with the plurality of processors, a memory for storing the programs may be provided for each processor or one memory may collectively store all the programs corresponding to all the processors.

(Operation of Medical Information Processing Apparatus)

The medical information processing apparatus 100 of the present embodiment is configured to use the trained model generated by machine learning for inferring the diagnosis result of the object (e.g., disease name and/or disease site) from the medical image(s) obtained by imaging the object. The medical images are, for example, a CT image, an MRI image and/or an ultrasonic image, which are stored in the image server or obtained by causing the modality 510 to image the object. In general, processing by machine learning can be divided into processing related to the training phase, in which a trained model is generated by training, and processing related to a running phase, in which the generated trained model is used.

In the training phase, the trained model is generated by supervised learning, i.e., by using plural training data, each of the plural training data includes a medical image and a ground truth accompanied to the medical image. In the medical image, an object-to-be-trained is depicted. The ground truth may be referred to as ground-truth data, correct data, or correct label.

In the medical information processing apparatus 100 of the present embodiment, in the training phase, attribute data of the objects-to-be-trained are acquired separately from the training data used for training. Details will be described below.

In the running phase, the medical images as the input data of an object to be diagnosed (hereafter, object-to-be-diagnosed) and the attribute data of the object-to-be-diagnosed are inputted to the medical information processing apparatus 100, and the inferred diagnosis result such as the disease name and the disease site of the object-to-be-diagnosed is outputted.

The processing circuitry 20 acquires the training data and attribute data of many objects-to-be-trained in the training phase, while acquiring object data (e.g., medical images) and attribute data of the object-to-be-diagnosed in the running phase, via the network interface circuit 10 of the medical information processing apparatus 100.

The processing circuitry 20 of the present embodiment implements the respective functions shown in FIG. 2, i.e., a training-data acquisition function 201, a training function 202, a first acquisition function 203, a second acquisition function 204, an input-data of object-to-be-diagnosed acquisition function 205, a goodness-of-fit calculation function 206, an application-method control function 207, a model processing function 208, and an alternative processing function 209. Each of these functions is implemented by causing the processor included in the processing circuits 20 to execute predetermined programs stored in the memory 30, for example.

Figure 3:
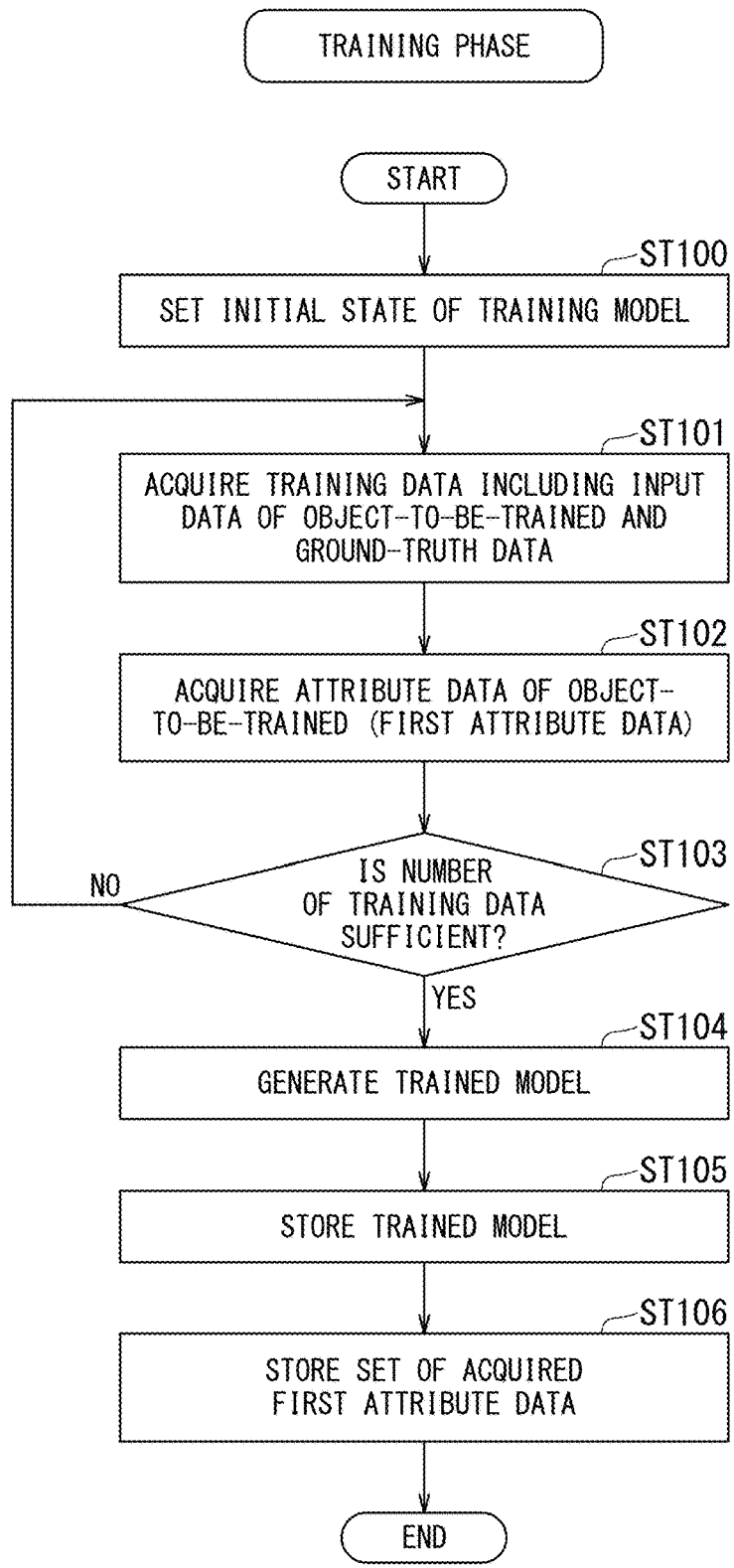
FIG. 3 is a flowchart illustrating an operation of a training phase of the medical information processing apparatus of the present embodiment.

Each of the above functions will be explained separately for the training phase and the running phase. FIG. 3 is a flowchart illustrating an operation in the training phase of the medical information processing apparatus 100 of the present embodiment. Further, FIG. 4A to FIG. 4D and FIG. 5A to FIG. 5D are schematic diagrams illustrating the operation concept of the training phase of the medical information processing apparatus 100 of the present embodiment. Hereinafter, the operation of each function of the medical information processing apparatus 100 will be described in detail along the flowchart of FIG. 3 by referring to FIGS. 4A to 4D and FIGS. 5A to 5D.

In the step ST100 of FIG. 3, the training model is set to the initial state. The processing of the step ST100 is performed by the training function 202, for example. In the step ST101, the training data composed of the input data of the object-to-be-trained and the ground-truth data are acquired.

The processing of the step ST101 is performed by the training-data acquisition function 201.

In the step ST102, the attribute data of the object-to-be-trained (i.e., the first attribute data) are acquired. The processing of the step ST102 is performed by the first acquisition function 203.

In the step ST103, it is determined whether the training-data acquisition processing is completed or not. For example, if it is determined that the number of training data is not sufficient to generate the trained model, the processing returns to the step ST101 and the acquisition of the training data and the first attribute data is continued. If it is determined that the number of training data is sufficient to generate the trained model, the processing proceeds to the step ST104.

In the above-described case, the training data acquisition processing is terminated based on the number of training data. However, instead of this method, the training data acquisition processing may be terminated when the estimation error or estimation accuracy of the output of the training model becomes equal to or lower than a predetermined value.

In the step ST104, the trained model 300 is generated on the basis of the acquired plurality of training data. In the next step ST105, the generated trained model 300 is stored in the memory 30. The training function 202 performs the processing of the steps ST104 and ST105.

In the step ST106, a set of the first attribute data acquired in the step ST102 is stored in the memory 30. The processing of the step ST106 is performed by the first acquisition function 203.

Figure 4A:
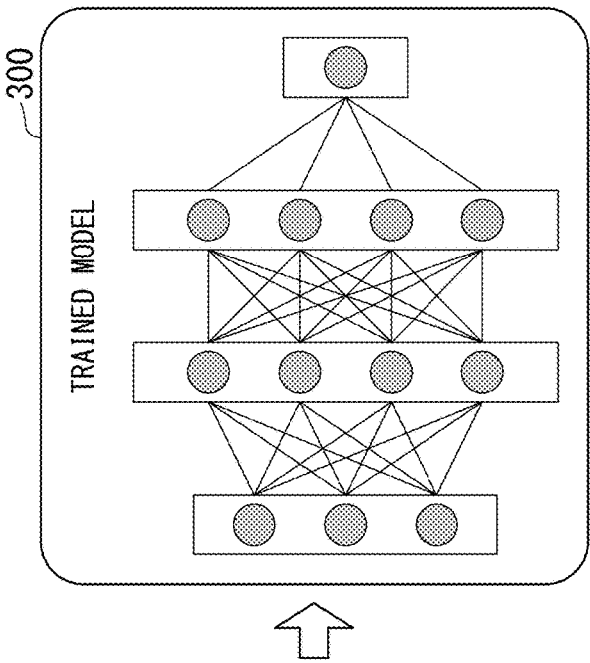
FIG. 4A to FIG. 4D are schematic diagrams illustrating an operation concept of the training phase.
Figure 4B:
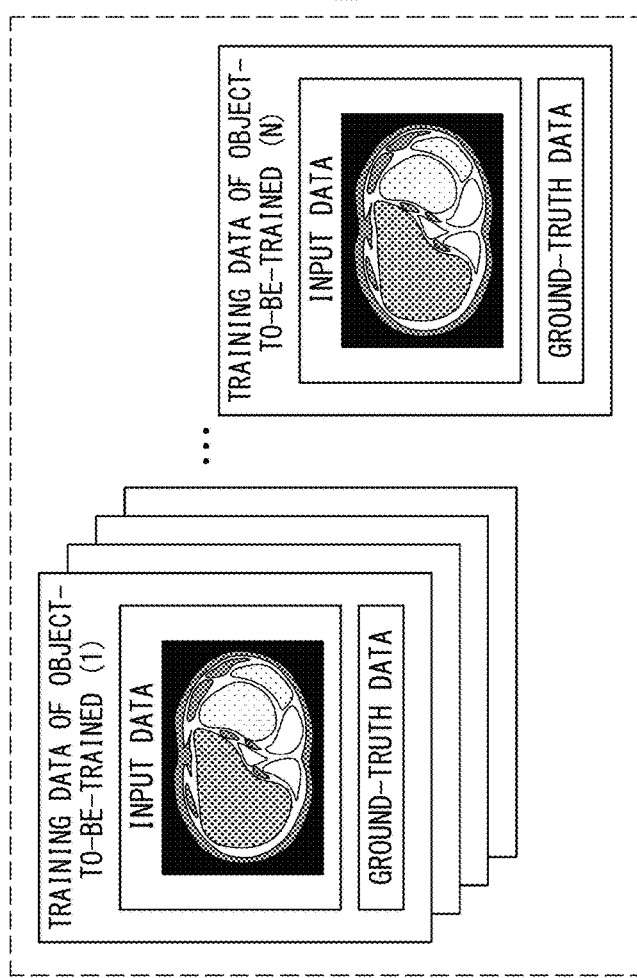

FIG. 4A to FIG. 4D are schematic diagrams illustrating the operation concept of the above-described training phase. FIG. 4A is a schematic diagram illustrating the concept of a plurality of training data used for training. The training data are composed of input data to the training model and ground-truth data attached to the input data. A typical example of the input data to the training model is a medical image such as a CT image and an MRI image. On the other hand, a typical example of the ground-truth data is finding data of a doctor or the like as a result of interpreting the medical image. For example, the ground-truth data may be a disease name or a disease site determined from the medical image.

In the case shown in FIG. 4A, it is shown that the trained model is generated from a plurality of training data that are composed of respective medical images of N objects of the object-to-be-trained (1) to the object-to-be-trained (N) and ground-truth data such as disease names and/or disease sites associated with the respective medical images.

Alternatively, biological information of the object can be used as the input data for generating the trained model instead of or in addition to the medical images. The biological information of the object is, for example, an electrocardiographic signal outputted from an electrocardiograph, a pulse wave signal outputted from a pulse wave meter, a respiratory signal and/or a body motion signal measured by using various sensors such as a pressure sensor.

The type of the machine learning algorithm used in the medical information processing apparatus 100 of the present embodiment and the trained model generated corresponding thereto are not limited to a specific type, and various methods may be adopted as the machine learning algorithms of the medical information processing apparatus 100. For example, as suggested in FIG. 4B, the medical information processing apparatus 100 may use a machine learning algorithm that uses a multi-layered neural network for classifying input data. Alternatively, the medical information processing apparatus 100 may use a machine learning algorithm that uses a support vector machine (SVM) for classifying input data. Additionally or alternatively, the medical information processing apparatus 100 may use a machine learning algorithm that classifies input data on the basis of decision trees using a tree-structured model or may use a random forest machine learning algorithm that aggregates the results of a plurality of decision trees and classifies the input data.

Figure 4C:
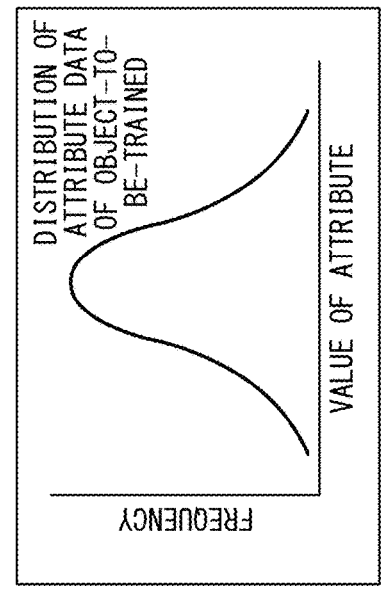
Figure 4D:
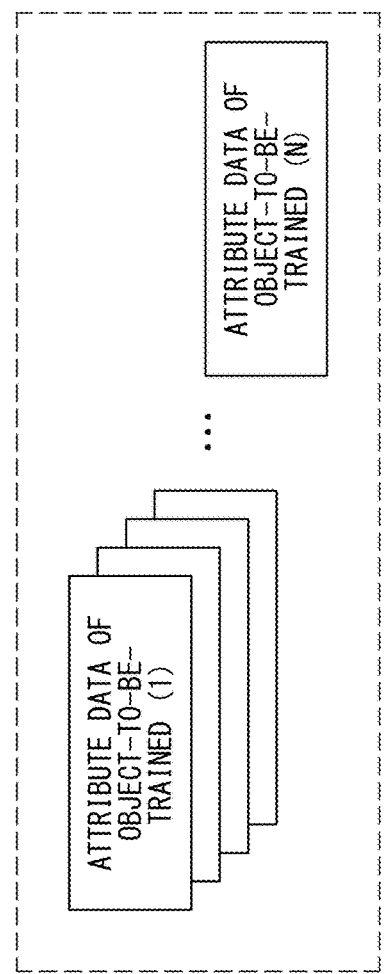

FIG. 4C shows that attribute data (i.e., the first attribute data) are acquired from the objects-to-be-trained (1) to (N), separately from the training data. It should be noted that although the attribute data is data indicating the attributes of the object-to-be-trained, they are not used for machine learning by themselves. In particular, the first attribute data are data indicating the characteristics of the population of the plurality of the objects-to-be-trained that have provided the input data used for generating the trained model.

There can be various types of characteristics of the population, i.e., various types of attribute data. For example, gender, birth area, and race of the object are also considered as types of the attribute data in addition to age, weight, height, a BMI value indicating obesity, blood pressure, indexes of triglycerides and cholesterol, various blood test values showing indicators of hepatic and renal functions, and urine test values such as urine protein can be considered as types of attribute data. Furthermore, the presence/absence of smoking and/or drinking habits, their degree, daily exercise amount, eating habits, and other types of lifestyle habits can also be considered as types of attribute data.

As shown in FIG. 4D or FIGS. 5B to 5D, from the acquired plurality of attribute data (i.e., first attribute data), a distribution of the attribute value, or a frequency of each attribute value can be calculated for each type of the attribute data. Further, statistics such as the mean value and standard deviation of each attribute data value can be calculated for each type of attribute data from the acquired plurality of attribute data.

For example, as illustrated in FIG. 5B and FIG. 5C, the distribution of age and/or body weight of the plurality of objects-to-be-trained can be calculated as the frequency of each values, i.e., as data showing the characteristics of the population of the objects used for training. In addition, as illustrated in FIG. 5D, when the birth areas of the respective objects-to-be-trained are aggregated as data showing the characteristics of the population of the objects used for training, the ratio or distribution of the birth areas of the plurality of objects-to-be-trained can be calculated.

The processing of classifying the plurality of attribute data into various types and calculating the distribution or the statistics for each type may be performed by the first acquisition function 203 or the goodness-of-fit calculation function 206 shown in FIG. 2.

Figure 6:
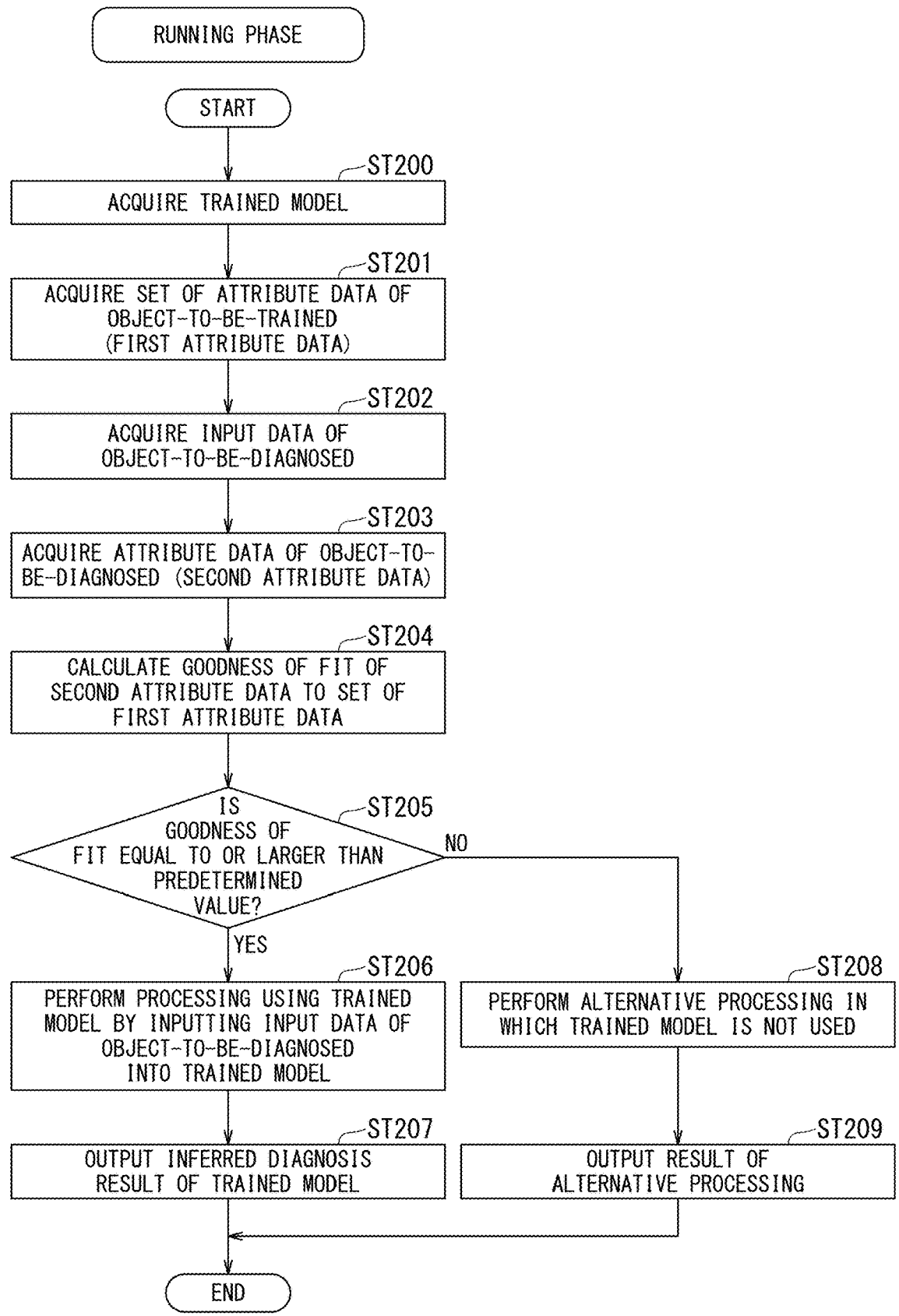
FIG. 6 is a flowchart illustrating an operation of a running phase of the medical information processing apparatus of the present embodiment.
Figure 7:
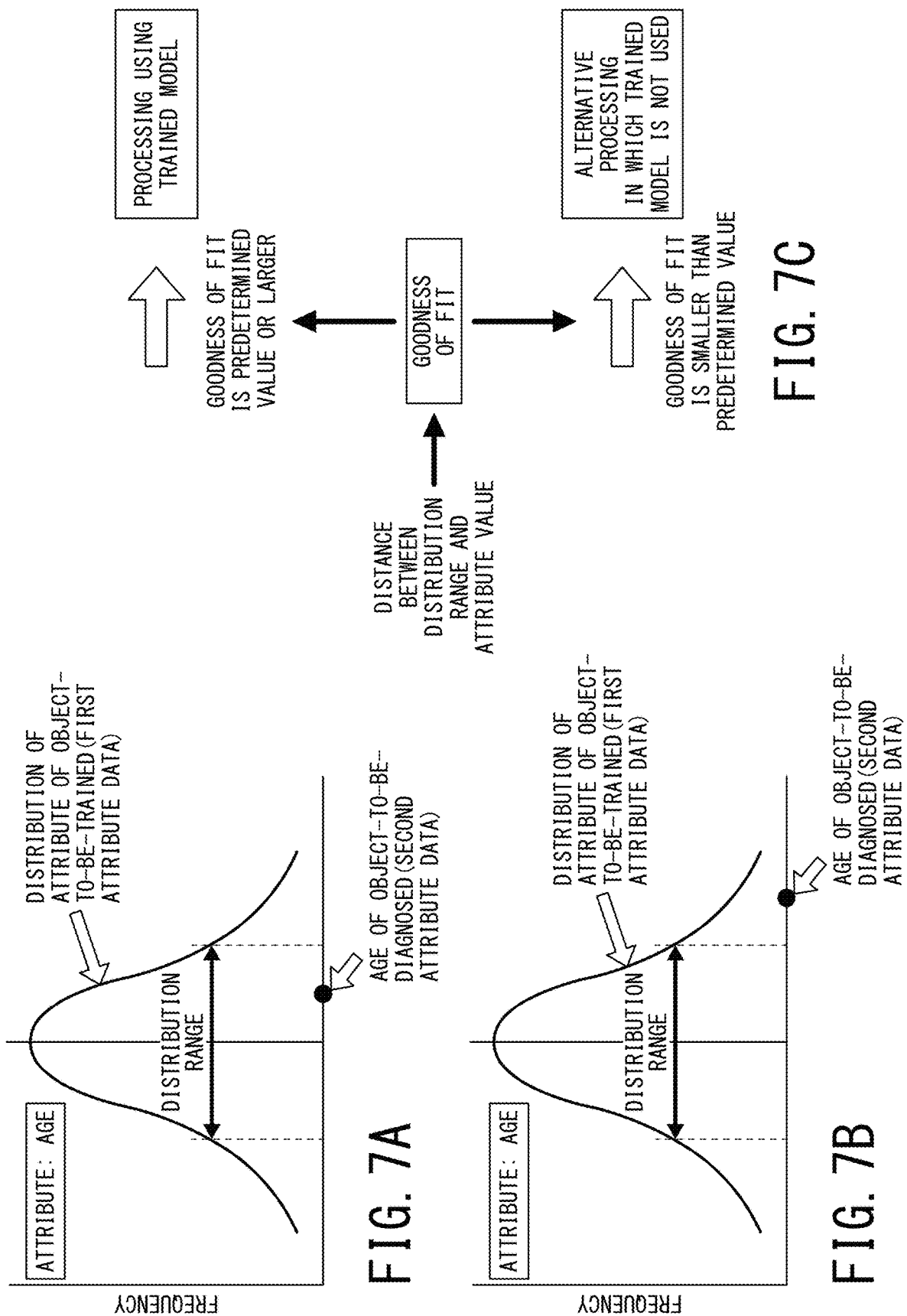
FIG. 7A to FIG. 7C are schematic diagrams specifically illustrating a first case of a method of calculating goodness of fit.
Figure 8:
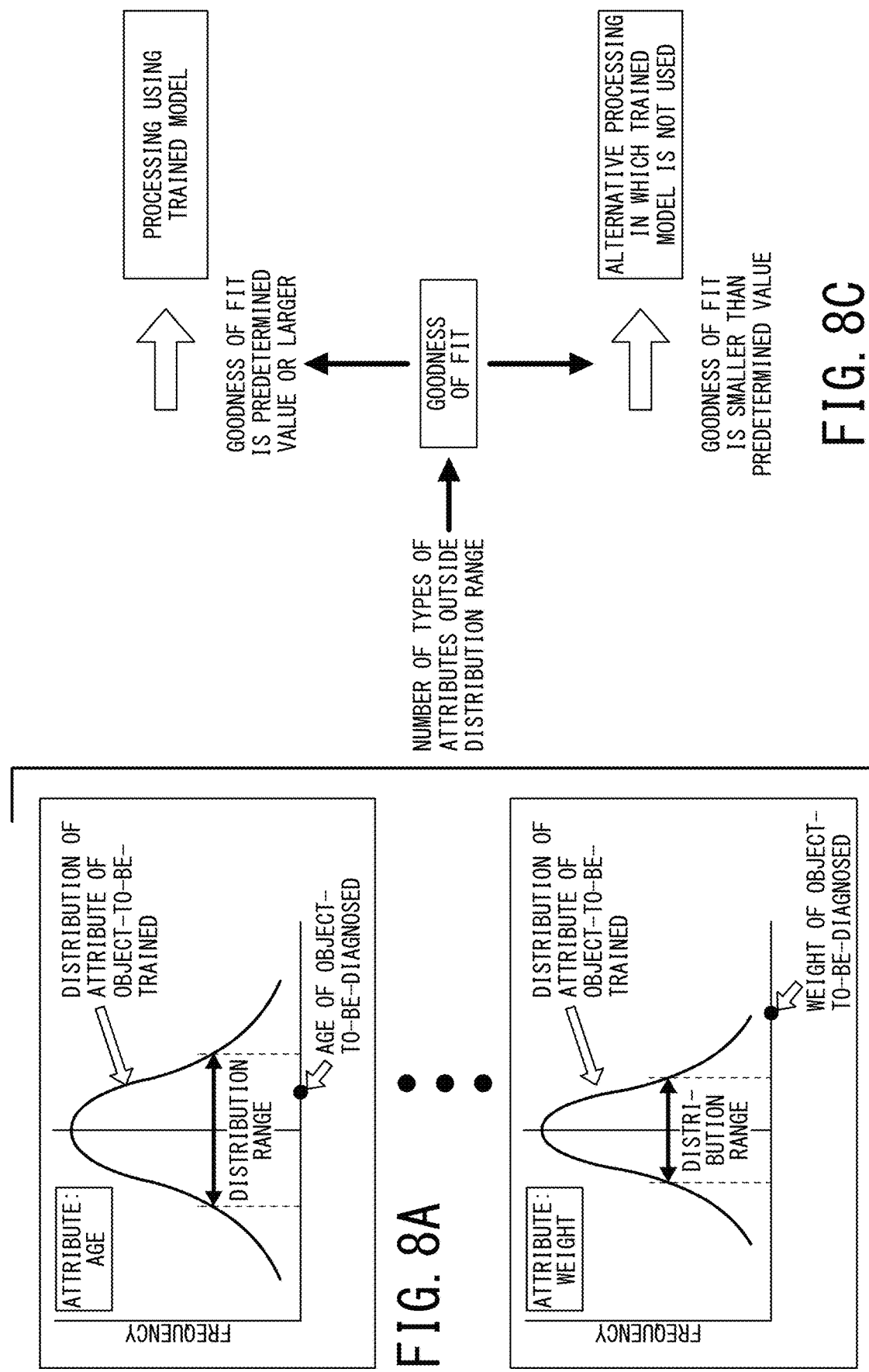
FIG. 8A to FIG. 8C are schematic diagrams specifically illustrating a second case of a method of calculating goodness of fit.

Next, the operation of the running phase will be described. FIG. 6 is a flowchart illustrating the operation in the running phase of the medical information processing apparatus 100 of the present embodiment. FIG. 7A to FIG. 10 are schematic diagrams illustrating the operation concept of the running phase of the medical information processing apparatus 100 of the present embodiment. Hereinafter, the operation of each function of the medical information processing apparatus 100 will be described in more detail on the basis of the flow of FIG. 6 by referring to FIG. 7A to FIG. 10.

In the step ST200, the trained model is acquired. Specifically, the trained model generated and stored in the training phase is acquired by, for example, reading out from the memory 30, and thus, the process using the trained model is made executable. The processing of the step ST200 is performed by the model processing function 208 shown in FIG. 2.

In the next step ST201, a set of attribute data (i.e., first attribute data) of the objects-to-be-trained are acquired by, for example, reading out from the memory 30. The processing of the step ST201 is performed by the goodness-of-fit calculation function 206 shown in FIG. 2. The processing of the steps ST200 and ST201 is processing in the preparation stage of the running phase, and the actual processing of the running phase is started from the step ST202.

In the step ST202, input data of an object-to-be-diagnosed is acquired from the modality 510 or the image server via the network interface circuit 10. Additionally or alternatively, the input data of the object-to-be-diagnosed may be acquired as data stored in a portable storage medium such as an optical disk and a USB memory via the network interface circuit 10.

The input data, which is acquired in the step ST202, is, for example, a medical image such as a CT image, an MRI image, or an ultrasonic image obtained by imaging the object-to-be-diagnosed. Note that the medical image acquired in the running phase is in the category equivalent or similar to the medical images used for generating the trained model in the training phase. Meanwhile, as described above, the trained model can be generated by using the biological information of the object such as the electrocardiographic signal and the respiratory signal instead of or in addition to the medical images. In this case, the biological information can be input data of the object-to-be-diagnosed acquired in the step ST202. The processing of the step ST202 is performed by the diagnosis-target input-data acquisition function 205 shown in FIG. 2.

In the next step ST203, the attribute data (i.e., the second attribute data) of the object-to-be-diagnosed is acquired. The second attribute data is data, which indicates the attribute of the object-to-be-diagnosed, and is associated with the input data such as the medical image of the object-to-be-diagnosed. The second attribute data belongs to the same category as the first attribute data and indicates the characteristics and attributes of the object-to-be-diagnosed. The characteristics and attributes of the object-to-be-diagnosed are, for example, age, weight, height, a BMI value indicating obesity, blood pressure, gender, birth area, and/or race. Alternatively or additionally, the characteristics and attributes of the object-to-be-diagnosed may be types of lifestyle, such as presence/absence of smoking and/or drinking habits and their degree, and/or degree of daily exercise. The processing of the step ST203 is performed by the second acquisition function 204 shown in FIG. 2.

In the next step ST204, a set of the first attribute data of the object-to-be-trained acquired in the step ST201 (i.e., a plurality of first attribute data) are compared with the attribute data of the object-to-be-diagnosed acquired in the step ST203 (i.e., the second attribute). The result of the comparison is used for calculating "goodness of fit", which is an index indicating the degree of matching of the second attribute data with the set of the first attribute data. The processing of the step ST204 is performed by the goodness-of-fit calculation function 206 shown in FIG. 2.

The higher the goodness of fit becomes, the higher the degree of matching of the second attribute data with the set of the first attribute data becomes. In other words, when the goodness of fit is high, the probability that the attribute of the object-to-be-diagnosed is included in the distribution of the population of the attribute of the objects-to-be-trained is sufficiently high. Conversely, the lower the goodness of fit becomes, the lower the degree of matching of the second attribute data with respect to the set of the first attribute data becomes, which indicates a lower probability that the attribute of the object-to-be-diagnosed is included in the distribution of the population of the attribute of the objects-to-be-trained. In other words, a lower goodness of fit indicates that the attribute of the object-to-be-diagnosed is significantly apart from the distribution of the population of the attributes of the objects-to-be-trained.

When the goodness of fit is low, the attributes of the objects for which the trained model is generated and the attribute of the object-to-be-diagnosed are different from each other. As a result, there is a possibility that the correct diagnostic result cannot always be inferred from this trained model. In other words, the diagnostic results obtained from this trained model may be unreliable.

In order to overcome the above-mentioned problem, in the medical information processing apparatus 100 of the present embodiment, the method of applying the input data of the object-to-be-diagnosed to the trained model is controlled based on the goodness of fit calculated in the step ST204. In other words, the processing to be performed on the input data of the object-to-be-diagnosed is controlled based on the calculated goodness of fit. Hereinafter, the calculation method of the goodness of fit and the application method to the trained model will be described specifically.

FIG. 7A to FIG. 7C are schematic diagrams illustrating a first case of a method of calculating the goodness of fit. In FIG. 7A to FIG. 7C, "age" is taken up as the type of attribute data. In the processing of the step ST204 for calculating the goodness of fit, the frequency for each attribute value (i.e., distribution of the attribute) is calculated from the set of the attribute data of the objects-to-be-trained (i.e., the plurality of first attribute data) acquired in the step ST201. For example, when the attribute is "age", the distribution is calculated such that the horizontal axis represents "age" and the vertical axis represents frequency thereof as illustrated in FIG. 7A and FIG. 7B.

As a parameter indicating the center and spread of the distribution, the average m of the "age" or the standard deviation $\sigma$ of the "age" may be calculated, respectively. In this case, "m±$\sigma$" or "m±2$\sigma$" can be considered as a "distribution range" of the values of the corresponding attributes, with the use of the average m and standard deviation $\sigma$.

In examples shown in FIG. 7A to FIG. 7C, the goodness of fit is calculated on the basis of the distance between the distribution range of the first attribute data and the second attribute data. For example, when the value of the second attribute data is defined as X, the ratio ($\sigma/|X-m|$) of the absolute value ($|X-m|$) of the difference between X and the average m of the distribution to the standard deviation $\sigma$ can be calculated as the goodness of fit.

Returning to FIG. 6, in the step ST205, it is determined whether the calculated goodness of fit satisfies the condition applicable to the training model or not. For example, the calculated goodness of fit is compared with a predetermined value (predetermined threshold value) to determine the magnitude of the goodness of fit. If the goodness of fit is equal to or larger than the predetermined value, it is determined that the goodness of fit satisfies the condition applicable to the training model. In the case of FIG. 7A to FIG. 7C, it is determined, for example, whether the goodness of fit is 1 or more ($\sigma/|X-m| \geq 1$?), i.e., whether the value X of the second attribute data is within the range of ±1$\sigma$ with respect to the average m of the distribution. Alternatively, it may be determined whether the goodness of fit is ½ or more ($\sigma/|X-m| \geq \frac{1}{2}$ ?), i.e., whether the value X of the second attribute data is within the range of $\pm 2\sigma$ with respect to the average m of the distribution. The processing of the step ST205 may be performed by the goodness-of-fit calculation function 206 shown in FIG. 2, or may be performed by the application-method control function 207.

FIG. 8A to FIG. 8C are schematic diagrams specifically illustrating second examples the method of calculating the goodness of fit. The above-described first example focuses on a particular attribute type (e.g., age), and the goodness of fit is calculated for this particular attribute on the basis of the distance between the distribution range of the first attribute data and the second attribute data.

On the other hand, the second example of the method of calculating the goodness of fit focuses on a plurality of types of attributes. Then, the distribution range of the first attribute data is calculated for each type of attribute. Further, the goodness of fit is calculated on the basis of the number of attribute types in each of which the value of the second attribute data (i.e., the value of the attribute of the object-to-be-diagnosed) is outside the above distribution range. Additionally or alternatively, the goodness of fit may be calculated on the basis of the ratio of total number of attribute types used for the determination to the number of attribute types outside the distribution range.

For example, assuming that the types of attributes used for determination are age", "weight", "height", "obesity degree", "blood pressure", and "blood glucose level". Among these types of the second attribute data used for determination, when "age" is the only type in which the value is out of the distribution range, the goodness of fit is calculated as, for example, 6 (=6/1). When three types including "age", "weight", and "height" are out of the distribution range, the goodness of fit is calculated as, for example, 2 (=6/3). According to such a calculation method, the smaller the number of types in which the value of the second attribute data is outside the distribution range becomes, the larger the goodness of fit of the second example becomes.

FIG. 9 is a schematic diagram illustrating a display screen SC1 for selecting the type of the attribute to be used for the determination. The display screen SC1 is displayed on the display 50. The type of attribute to be used for the determination can be set by clicking the "select" button after the user puts a check mark on the desired attribute, for example.

The goodness of fit is not limited to the above-described particular examples, and various methods of calculating the goodness of fit can be adopted. For example, for each of the plurality of types of attributes selected by using the display screen SC1 shown in FIG. 9, the distance between the distribution range of the first attribute data and the second attribute data is calculated. The calculated distance may be subjected to weighted addition depending on the type of attribute, and then the goodness of fit can be calculated based on the result of the weighted addition.

As another method, for example, the goodness of fit is binarized or set to 2 values (0 or 1) instead of continuous values. Then, for example, among the one or more types of attributes selected using the display screen SC1 shown in FIG. 9, if at least one attribute type which distance between the distribution range of the first attribute data and the second attribute data is the predetermined value or larger, the goodness of fit is set to "0". In other cases, the goodness of fit is set to "1".

Note that, depending on the type of attribute, the value of the attribute may not be expressed as a continuous value in the first place, such as "gender", "birth area", and "race". Even in such a case, the goodness of fit can be calculated by binarizing the goodness of fit. For example, when the attribute type is "birth area", the value of the attribute may be "Japan", "Africa", "Europe" or the like. In this case, first, the value having the highest frequency of the attribute value of the first attribute data is obtained. Then, when the obtained value and the attribute value of the second attribute data match, the goodness of fit is set to "1", and when they do not match, the goodness of fit is set to "0". For example, when the value having the highest frequency of the attribute value of the first attribute data is "Japan" and the attribute value of the second attribute is also "Japan", the goodness of fit is set to "1"; on the other hand, when the attribute value of the second attribute is "Africa", the goodness of fit is set to "0". The application-method control function 207 in FIG. 2 controls the processing to be performed on the input data of the object-to-be-diagnosed. For example, the application-method control function 207 controls the method of applying the input data of the object-to-be-diagnosed to the trained model 300 on the basis of the goodness of fit. Note that the method of application of the input data of the object-to-be diagnosed to the trained model 300 not only includes a method of inputting the input data into the trained model 300, but also includes a method of processing the input data by other alternative processing in which the trained model 300 is not used.

Returning to FIG. 6, if it is determined in the step ST205 that the calculated goodness of fit is larger than or equal to the predetermined value, the processing proceeds to the step ST206, in which the normal machine learning algorithm is executed. The processing of the step ST206 is performed by the application-method control function 207 and the model processing function 208 shown in FIG. 2. That is, if it is determined that the calculated goodness of fit is equal to or larger than the predetermined value, the application-method control function 207 determines that it is appropriate to process the input data of the object-to-be-diagnosed with the trained model 300, and passes the input data of the object-to-be-diagnosed to the model processing function 208. Afterward, the model processing function 208 inputs the input data of the object-to-be-diagnosed into the trained model 300, and performs processing using the trained model 300.

Figure 10:
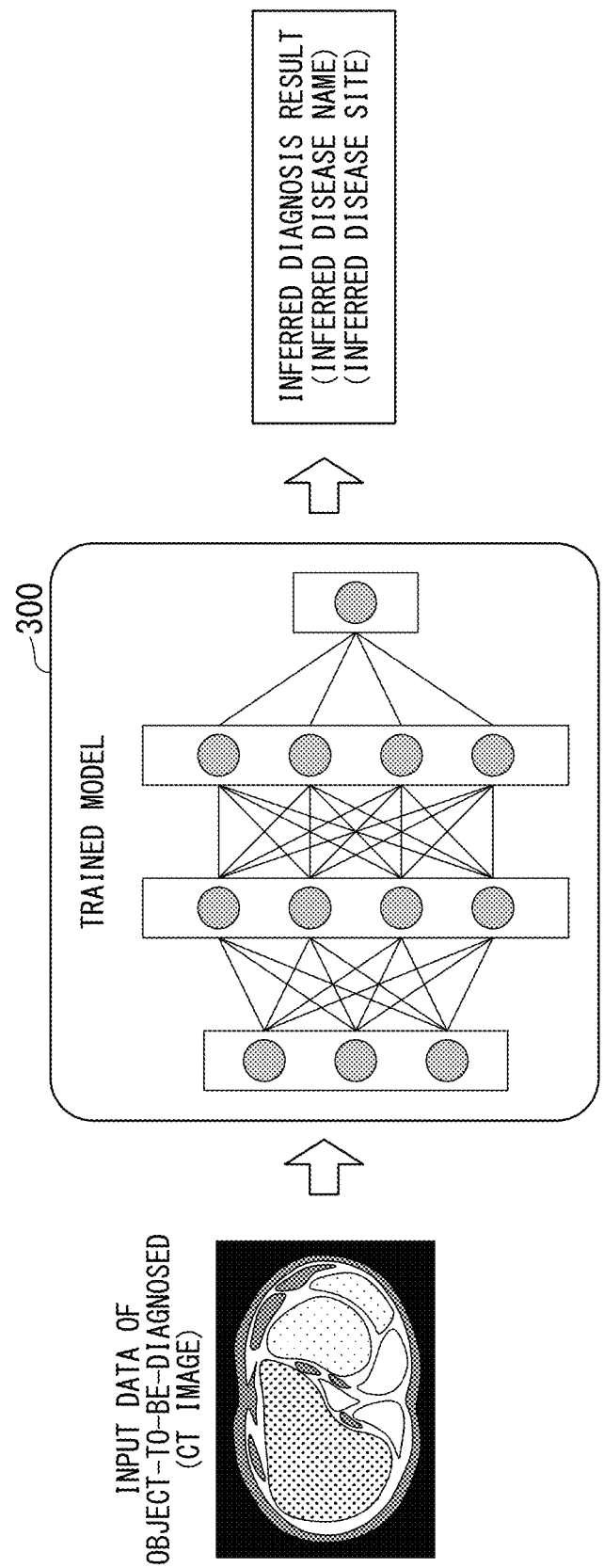
FIG. 10 is a schematic diagram illustrating a processing concept using a trained model.

FIG. 10 is a schematic diagram illustrating a processing concept using the trained model 300. As shown in FIG. 10, the input data of the object-to-be-diagnosed such as a CT image of the object-to-be-diagnosed is inputted to the trained model 300, and the inferred diagnosis result such as the inferred disease name and/or the inferred disease site of the object is outputted from the trained model 300. The inferred diagnosis result outputted from the trained model 300 is, for example, displayed on the display 50 in the step ST207 for supporting the final diagnosis by a doctor.

When it is determined in the ST205 that the calculated goodness of fit is smaller than the predetermined value, warning information indicating the determination result may be outputted, although not explicitly shown in FIG. 6. The warning information may be displayed on the display 50, or the medical information processing apparatus 100 may be configured to warn the user with voice information, for example. After outputting the warning information, the processing may proceed to the step ST206 to execute the normal machine learning algorithm.

Meanwhile, when it is determined that the goodness of fit calculated in the ST205 is smaller than the predetermined value, the processing may proceed to the step ST208 after issuing the warning information or may proceed to the step ST208 without issuing the warning information.

In the step ST208, alternative processing in which the trained model is not used is performed. The processing of the step ST208 is performed by the application-method control function 207 and the alternative processing function 209 shown in FIG. 2.

The alternative processing without using the trained model includes processing that performs known computer-aided diagnosis (CAD) that is not based on machine learning. The alternative processing in this case (i.e., the processing of performing known CAD is performed by the alternative processing function 209 shown in FIG. 2. The result of the alternative processing is outputted from the medical information processing apparatus 100 in the step ST209. For example, the result of the alternative processing is displayed on the display 50.

As alternative processing, the display 50 may display some of known computer-aided diagnosis (CAD) methods, which are not based on machine learning and can be processed by the medical information processing apparatus 100, so that the user is allowed to select a desired one from the displayed choices.

As further alternative processing, the medical information processing apparatus 100 may perform a display of prompting the user to visually diagnose the medical image by himself/herself, or perform a display of introducing another medical institution.

When the attribute of the population of the objects used for generating the trained model is different from the attribute of the object-to-be-diagnosed, the inference using the trained model may not provide a correct diagnosis result. However, the medical information processing apparatus 100 of the present embodiment calculates the goodness of fit, which is an index indicating the matching degree of the attribute of the object-to-be-diagnosed with the attributes of the population used for generating the trained model. And then, when this goodness of fit is smaller than the predetermined value, the medical information processing apparatus 100 presents warning information to the user or provides other alternative processing that does not use the trained model. Consequently, the medical information processing apparatus 100 of the present embodiment can reduce the possibility of providing erroneous diagnostic support information even if the population of the data used in the training phase of machine learning is different in attribute from the population of the data to be used in the running phase.

As described so far, the medical information processing apparatus 100 has both the processing function of the training phase and the processing function of the running phase, as shown in FIG. 2. That is, the medical information processing apparatus 100 has a function of generating a trained model. However, embodiments of the present invention are not limited to such an aspect. The medical information processing apparatus 100 of the present embodiment may be configured to acquire the trained model generated by another apparatus from the outside and substantially have only the processing function of the running phase. In this case, the medical information processing apparatus 100 of the present embodiment can obtain the above-described technical effects by acquiring the trained model from the outside and acquiring a set of attribute data of the objects-to-be-trained used for generating this trained model.

Further, as described so far, the medical images and/or biological information of the object-to-be-diagnosed are used to obtain the trained model to infer the disease name and disease site of the object. However, the medical information processing apparatus 100 of the present embodiment is not limited to this aspect. For example, the medical information processing apparatus 100 can perform machine learning so as to generate a trained model that acquires raw data such as projection data for reconstructing a CT image and k-space data for reconstructing an MRI image as input and outputs a reconstructed image from these raw data. When such a trained model is generated in the training phase, and the raw data of the object-to-be-diagnosed are inputted into the trained model in the running phase, a reconstructed image of the object-to-be-diagnosed can be outputted. Even in such reconstruction processing, when the population of the object-to-be-trained that has provided the raw data in the training phase is different in attribute from the object-to-be-diagnosed, a reconstruction image with poor image quality may be generated. However, such deterioration of the image quality of the reconstructed image can be prevented by applying the characteristics of the above-described embodiments to the reconstruction processing. For example, when the population of the objects-to-be-trained is different in attribute from the object-to-be-diagnosed, conventional known reconstruction processing may be executed as alternative processing instead of the reconstruction processing based on machine learning, which prevents deterioration in image quality.

According to at least one embodiment described above, even when the population of the data used in the training phase of machine learning is different in attribute from the population of data to be used in the running phase, the possibility of providing erroneous diagnostic support information can be reduced.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical information processing apparatus comprising:
    processing circuitry configured to:
        perform processing using a trained model that is generated by machine learning with a plurality of training data;
        acquire first attribute data indicating at least one attribute of an object-to-be-trained related to the plurality of training data that are used for generating the trained model;
        acquire second attribute data indicating at least one attribute of an object-to-be-diagnosed; and
        perform the processing using the trained model based on goodness of fit that is an index indicating degree of matching between the first attribute data and the second attribute data, wherein
    the at least one attribute of the object-to-be-trained comprises a plurality of types of attributes; and
    the goodness of fit is determined based on (i) a distribution range of the first attribute data calculated for each of the plurality of types of attributes of the object-to-be-trained and (ii) number of types of attributes for which the second attribute data are outside the distribution range.

2. The medical information processing apparatus according to claim 1, wherein the processing circuitry is further configured to:
input at least one of a medical image and biological information of the object-to-be-diagnosed into the trained model; and
output an inferred diagnosis result of the object-to-be-diagnosed.

3. The medical information processing apparatus according to claim 2, wherein the processing circuitry is further configured to:
input input-data of the object-to-be-diagnosed into the trained model and perform the processing using the trained model when the goodness of fit satisfies a fitting condition that fits the trained model; and
perform processing of issuing a warning to a user or other alternative processing when the goodness of fit does not satisfy the fitting condition, the alternative processing being processing that does not use the trained model.

4. The medical information processing apparatus according to claim 3, wherein the alternative processing includes processing of performing computer-aided diagnosis that is not based on the machine learning.

5. The medical information processing apparatus according to claim 3, wherein the alternative processing includes (i) processing related to a display suggesting that a user should visually diagnose the medical image or (ii) processing related to a display that introduces another medical institution.

6. The medical information processing apparatus according to claim 1, wherein the goodness of fit is calculated based on distance between a distribution range of the first attribute data and the second attribute data.

7. The medical information processing apparatus according to claim 1, wherein types of the at least one attribute of the object-to-be-trained includes at least one of age, gender, body weight, race, area of birth, type of lifestyle, and a blood test value.

8. The medical information processing apparatus according to claim 1, wherein the processing circuitry is further configured to:
input imaging raw data of the object-to-be-diagnosed into the trained model; and
output a reconstructed image of the object-to-be-diagnosed.

9. A medical information processing apparatus comprising:
processing circuitry configured to:
perform processing using a trained model that is generated by machine learning with a plurality of training data;
acquire first attribute data indicating at least one attribute of an object-to-be-trained related to the plurality of training data that are used for generating the trained model;
acquire second attribute data indicating at least one attribute of an object-to-be-diagnosed; and
perform the processing using the trained model based on goodness of fit that is an index indicating degree of matching between the first attribute data and the second attribute data, wherein
the at least one attribute of the object-to-be-trained comprises a plurality of types of attributes; and
the processing circuitry is configured to perform processing of issuing a warning to a user or other alternative processing when the at least one attribute of the object-to-be-diagnosed is a specific attribute and the goodness of fit of the specific attribute is equal to or less than a predetermined value, the alternative processing being processing that does not use the trained model.

10. A medical information processing method comprising:
performing processing using a trained model that is generated by machine learning with a plurality of training data;
acquiring first attribute data indicating at least one attribute of an object-to-be-trained related to the plurality of training data that are used for generating the trained model;
acquiring second attribute data indicating an attribute of an object-to-be-diagnosed; and
performing the processing on input-data of the object-to-be-diagnosed based on goodness of fit that is an index indicating degree of matching between the first attribute data and the second attribute data, wherein
the at least one attribute of the object-to-be-trained comprises a plurality of types of attributes; and
the goodness of fit is determined based on (i) a distribution range of the first attribute data calculated for each of the plurality of types of attributes of the object-to-be-trained and (ii) number of types of attributes for which the second attribute data are outside the distribution range.

11. A medical information processing method comprising:
performing processing using a trained model that is generated by machine learning with a plurality of training data;
acquiring first attribute data indicating at least one attribute of an object-to-be-trained related to the plurality of training data that are used for generating the trained model;
acquiring second attribute data indicating an attribute of an object-to-be-diagnosed; and
performing the processing on input-data of the object-to-be-diagnosed based on goodness of fit that is an index indicating degree of matching between the first attribute data and the second attribute data, wherein
the at least one attribute of the object-to-be-trained comprises a plurality of types of attributes; and
the method further comprises performing processing of issuing a warning to a user or other alternative processing when the at least one attribute of the object-to-be-diagnosed is a specific attribute and the goodness of fit of the specific attribute is equal to or less than a predetermined value, the alternative processing being processing that does not use the trained model.

* * * * *